United States Patent [19]

Holtkamp, Sr.

[11] Patent Number: Plant 6,536

[45] Date of Patent: Jan. 17, 1989

[54] AFRICAN VIOLET PLANT NAMED CAROLYN

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,473

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Carolyn, characterized by its bright, relatively dark pink, violet-shaped single flowers; tight bouquet above the leaves on strong upright flower stems; profuse flowering; vigorous growth habit; dark green, sometimes serrated, velvety leaves; and long lasting and non-dropping flowering habit.

1 Drawing Sheet

The present invention comprises a new and distinct cultivar of African violet plant, botanically known as *Saintpaulia ionantha,* and hereinafter referred to by the cultivar named Carolyn.

The new cultivar Carolyn was discovered by applicant in 1985 in Haffen, Federal Republic of Germany, while growing as a single plant among plants of the parent cultivar Arkansas, disclosed in U.S. Plant Pat. No. 5,725. The new cultivar was immediately recognized by its dark pink flower color, as compared to the red-purple flower color of its parent, and was given the selection number M68/47. The parent cultivar Arkansas was developed in a breeding program in Isselburg, Federal Republic of Germany from a female parent identified as XX4256 blue single and a male parent identified as XX 4158 purplish red.

Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Carolyn has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Carolyn which in combination distinguish this african violet as a new and distinct cultivar:

1. Bright, relatively dark pink, violet-shaped single flowers.
2. First flash of flowers forms a tight bouquet above the leaves on strong upright flower stems.
3. Long-lasting, non-dropping flowers.
4. Each plant carries 10–12 and more upright flower stems, each of which carries 10–12 and more flowers.
5. Profuse flowering.
6. Seed capsule pushes slightly through.
7. Vigorous grower.
8. Plant saleable 10–11 weeks after potting.

9. Dark green, sometimes serrated, velvety leaves.
10. After maturity, the flowers dry off and remain on the peduncle without becoming infected by botrytis.

The new cultivar is most similar to its parent Arkansas. Carolyn is principally distinguished from Arkansas by its bright pink flower color and more profuse flowering habit, although other differences exist.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 1:00 p.m. in Nashville, Tenn. Under color growing conditions and more intensive lighting, the dark pink color becomes more intense.

Botanical classification: *Saintpaulia ionantha,* Ramat., cv. Carolyn.

Propagation: The new cultivar holds its distinguishing characteristics through successive propagations by leaf cuttings and by division of shoots.

Plant: From 10 cm to 12 cm tall when grown in pots, and approximately 25–30 cm in diameter when fully grown. The growth rate is vigorous.

*Leaves.*—Shape: Oval. Diameter: 60–70 mm wide and 75–85 mm long. Texture: Velvety. Aspect: Some plants very serrated, some no serration, hairy. Ribs and Veins: Upperside visible, underside very well pronounced, purplish green and shiny. Color (upper side): Green 139A. Color (under side): Red purple 70A, slightly lighter greenish veins. Petioles: Strong, upright, purplish, hairy.

*Flowers.*—Buds: Bell-shaped, 8–10 mm before opening. Sepals: Five (5) in number, purplish-brown. Calyx: Funnel-shaped. Aspect: Spear-shaped, hairy. Peduncle: Strong, upright, purplish brown, hairy.

*Individual flowers.*—Size: Approximately 40 mm. Shape: Single violet-shaped, slightly waved. Color (upper side): Exact color is difficult to value; closest approximation is red purple 74, between B and D; center or throat is darker, approximately 74A, and this darker color radiates irregularly from center. Color (under side): Red purple 74C. Borne: Each flower stem carries 10–12 flowers on strong, upright, wire-like, peduncles that are free standing above the leaves. Flowering habit: Flowers 9–10 weeks after potting. Corolla: Compact flower head.

*Reproductive organs.*—Stamens: Two (2) in number. Anthers: Two stamens composed of 4 anther cells. Filaments: 4 mm long, yellowish green. Pollen Color: Yellow 7A. Styles: 8 mm, dark pink.

*Roots.*—Normally developed, white when young, turning slightly brownish when older.

Disease resistance: Good.

General observations: Carolyn is a vigorous grower, with attractive dark green leaves which are normally serrated. Out of the center, 10–12 and more strong flower stems appear that are slightly bending toward the center, carrying 10–12 and more single, violet-shaped flowers. The flowers are bright medium to dark pink; the center is slightly darker and this darker tone radiates into the 2 smaller petals. Approximately 10–11 weeks after potting the plant is saleable. The flowers are long-lasting and non-dropping and the seed capsule pushes through.

I claim:

1. A new and distinct cultivar of African violet named Carolyn, as described and illustrated, and particularly characterized by its bright, relatively dark pink, violet-shaped single flowers; tight bouquet above the leaves on strong upright flower stems; profuse flowering; vigorous growth habit; dark green, sometimes serrated, velvety leaves; and long lasting and non-dropping flowering habit.

* * * * *

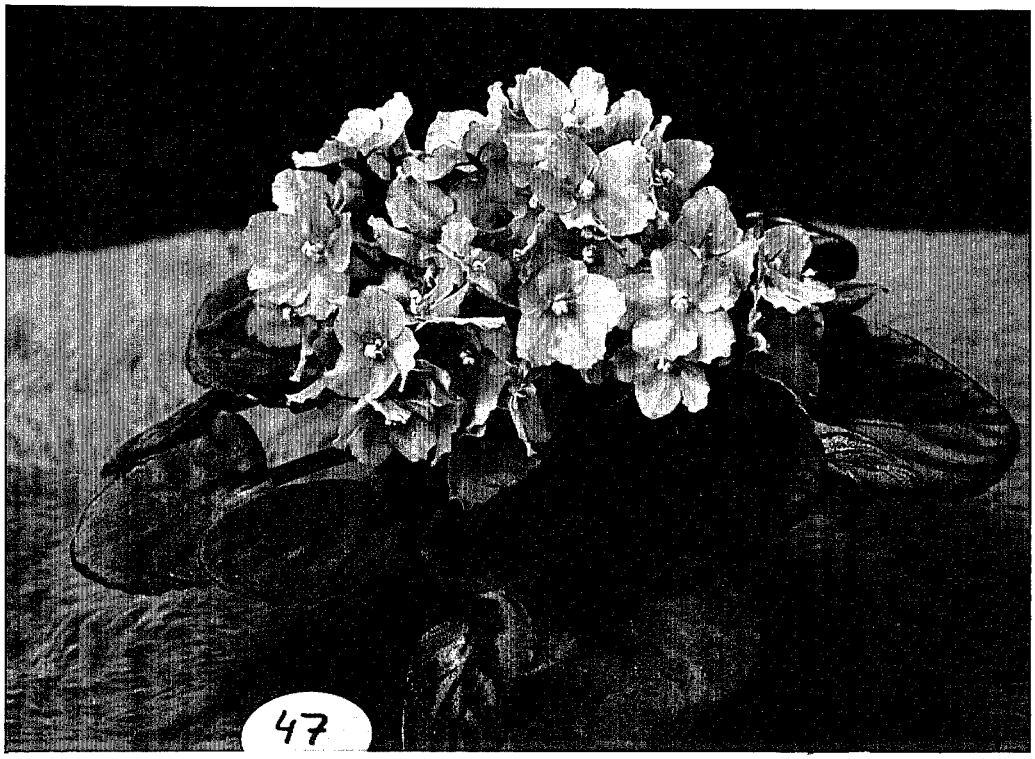
47